United States Patent
Shuros et al.

(10) Patent No.: US 12,310,652 B2
(45) Date of Patent: May 27, 2025

(54) HYBRID ELECTROPORATION ABLATION CATHETER

(71) Applicant: Boston Scientific Scimed, Inc., Maple Grove, MN (US)

(72) Inventors: Allan C. Shuros, St Paul, MN (US); Brendan E. Koop, Ham Lake, MN (US); Michael S. Coe, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 304 days.

(21) Appl. No.: 17/383,092

(22) Filed: Jul. 22, 2021

(65) Prior Publication Data

US 2023/0026265 A1 Jan. 26, 2023

Related U.S. Application Data

(60) Provisional application No. 63/056,300, filed on Jul. 24, 2020.

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/00196* (2013.01);
(Continued)

(58) Field of Classification Search
CPC ...... A61B 18/1492; A61B 2018/00196; A61B 2018/00267; A61B 2018/00577;
(Continued)

(56) References Cited

U.S. PATENT DOCUMENTS

| 4,200,104 A | 4/1980 | Harris |
| 4,470,407 A | 9/1984 | Hussein |

(Continued)

FOREIGN PATENT DOCUMENTS

| AU | 741167 B2 | 11/2001 |
| EP | 1042990 A1 | 10/2000 |

(Continued)

OTHER PUBLICATIONS

Du Pre, B.C. et al., "Minimal coronary artery damage by myocardial electroporation ablation," Europace, 15(1): 144-149 (2013).
(Continued)

*Primary Examiner* — Jaymi E Della
(74) *Attorney, Agent, or Firm* — Nelson Mullins Riley & Scarborough LLP

(57) ABSTRACT

At least some embodiments of the present disclosures are directed to a hybrid electroporation ablation catheter. In some embodiments, the hybrid electroporation ablation catheter comprises a catheter shaft having a proximal end and an opposite distal end and an electrode assembly extending from the distal end of the catheter shaft and the electrode assembly comprising a plurality of energy-delivering electrodes. The electrode assembly is configured to be selectively operable in a plurality of different operation modes.

5 Claims, 6 Drawing Sheets

(52) U.S. Cl.
CPC ............ *A61B 2018/00267* (2013.01); *A61B 2018/00577* (2013.01); *A61B 2018/00613* (2013.01); *A61B 2018/00702* (2013.01); *A61B 2018/124* (2013.01); *A61B 2018/126* (2013.01); *A61B 2018/1467* (2013.01); *A61B 2018/1475* (2013.01)

(58) Field of Classification Search
CPC .... A61B 2018/00613; A61B 2018/124; A61B 2018/126; A61B 2018/1467; A61B 2018/1475; A61B 5/6858
See application file for complete search history.

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | Deford et al. |
| 5,306,296 A | 4/1994 | Wright et al. |
| 5,313,943 A * | 5/1994 | Houser ............. A61B 5/6858 606/41 |
| 5,334,183 A | 8/1994 | Wuchinich |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho et al. |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,860,974 A | 1/1999 | Abele |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 5,938,660 A | 8/1999 | Swartz et al. |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,142,993 A | 11/2000 | Whayne et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,109 B1 | 6/2001 | Hassett et al. |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | Mcgovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | Mcgovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Toellner et al. |
| 6,607,520 B2 | 8/2003 | Keane |
| 6,613,046 B1 | 9/2003 | Jenkins et al. |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless et al. |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |

(56) References Cited

U.S. PATENT DOCUMENTS

| | | |
|---|---|---|
| 7,207,989 B2 | 4/2007 | Pike et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | De et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,842,031 B2 | 11/2010 | Abboud et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Ee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,568,410 B2 | 10/2013 | Vakharia et al. |
| 8,571,635 B2 | 10/2013 | Mcgee |
| 8,571,647 B2 | 10/2013 | Harlev et al. |
| 8,579,897 B2 | 11/2013 | Vakharia et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emmons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 8,996,091 B2 | 3/2015 | De et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,113,911 B2 | 8/2015 | Sherman |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,204,916 B2 | 12/2015 | Lalonde |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,351,789 B2 | 5/2016 | Novichenok et al. |
| 9,375,268 B2 | 6/2016 | Long |
| 9,387,031 B2 | 7/2016 | Stewart et al. |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,510,888 B2 | 12/2016 | Jean-Pierre |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |

(56) References Cited

U.S. PATENT DOCUMENTS

| | | |
|---|---|---|
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,801,681 B2 | 10/2017 | Laske et al. |
| 9,808,304 B2 | 11/2017 | Lalonde |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,010,368 B2 | 7/2018 | Laske et al. |
| 10,016,232 B1 | 7/2018 | Bowers et al. |
| 10,130,423 B1* | 11/2018 | Viswanathan ..... A61B 18/1492 |
| 10,172,673 B2 | 1/2019 | Viswanathan et al. |
| 10,194,818 B2 | 2/2019 | Williams et al. |
| 10,285,755 B2 | 5/2019 | Stewart et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,512,505 B2 | 12/2019 | Raju |
| 10,512,779 B2 | 12/2019 | Viswanathan et al. |
| 10,517,672 B2 | 12/2019 | Long |
| 10,617,467 B2 | 4/2020 | Viswanathan et al. |
| 10,660,702 B2 | 5/2020 | Viswanathan et al. |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0022839 A1 | 2/2002 | Stewart et al. |
| 2002/0052602 A1 | 5/2002 | Wang et al. |
| 2002/0058933 A1 | 5/2002 | Christopherson et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Prestel |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0060856 A1 | 3/2003 | Chornenky et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek-Petric |
| 2003/0229379 A1 | 12/2003 | Maynard |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Chrisitian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0112349 A1* | 5/2007 | Danek .................. A61B 90/30 606/45 |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Sliwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076496 A1 | 3/2009 | Azure |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |

(56) References Cited

U.S. PATENT DOCUMENTS

| | | |
|---|---|---|
| 2011/0106221 A1 | 5/2011 | Neal et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Hue-Teh |
| 2014/0051993 A1 | 2/2014 | Mcgee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0200578 A1* | 7/2014 | Groff ................ A61B 18/1492 606/41 |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0253140 A1 | 9/2014 | Gilbert |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0141982 A1 | 5/2015 | Lee |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |

(56) References Cited

U.S. PATENT DOCUMENTS

| | | |
|---|---|---|
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220305 A1* | 8/2016 | Deem ............... A61B 18/1492 |
| 2016/0220307 A1 | 8/2016 | Miller et al. |
| 2016/0235470 A1 | 8/2016 | Callas et al. |
| 2016/0249972 A1 | 9/2016 | Klink |
| 2016/0256682 A1 | 9/2016 | Paul et al. |
| 2016/0278660 A1 | 9/2016 | Nagale et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelson et al. |
| 2016/0331441 A1 | 11/2016 | Konings |
| 2016/0331459 A1 | 11/2016 | Townley et al. |
| 2016/0338770 A1 | 11/2016 | Bar-Tal et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1* | 4/2017 | Cao .................. A61N 1/325 |
| 2017/0120048 A1 | 5/2017 | He et al. |
| 2017/0146584 A1 | 5/2017 | Daw et al. |
| 2017/0151014 A1 | 6/2017 | Perfler |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0189106 A1 | 7/2017 | Schuler et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0028252 A1 | 2/2018 | Lalonde |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0161093 A1 | 6/2018 | Basu et al. |
| 2018/0168511 A1 | 6/2018 | Hall et al. |
| 2018/0184982 A1 | 7/2018 | Basu et al. |
| 2018/0193090 A1 | 7/2018 | De et al. |
| 2018/0200497 A1 | 7/2018 | Mickelsen |
| 2018/0235496 A1 | 8/2018 | Wu et al. |
| 2018/0256109 A1 | 9/2018 | Wu et al. |
| 2018/0280080 A1 | 10/2018 | Govari et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344202 A1 | 12/2018 | Bar-Tal et al. |
| 2018/0344393 A1 | 12/2018 | Gruba et al. |
| 2018/0360531 A1 | 12/2018 | Holmes et al. |
| 2018/0360534 A1 | 12/2018 | Teplitsky et al. |
| 2019/0015007 A1 | 1/2019 | Rottmann et al. |
| 2019/0015638 A1 | 1/2019 | Gruba et al. |
| 2019/0030328 A1 | 1/2019 | Stewart et al. |
| 2019/0046791 A1 | 2/2019 | Ebbers et al. |
| 2019/0069949 A1 | 3/2019 | Vrba et al. |
| 2019/0069950 A1 | 3/2019 | Viswanathan et al. |
| 2019/0076179 A1 | 3/2019 | Babkin et al. |
| 2019/0125439 A1 | 5/2019 | Rohl et al. |
| 2019/0125788 A1 | 5/2019 | Gruba et al. |
| 2019/0143106 A1 | 5/2019 | Dewitt et al. |
| 2019/0151015 A1 | 5/2019 | Viswanathan et al. |
| 2019/0175263 A1 | 6/2019 | Altmann et al. |
| 2019/0183378 A1 | 6/2019 | Mosesov et al. |
| 2019/0183567 A1 | 6/2019 | Govari et al. |
| 2019/0192223 A1 | 6/2019 | Rankin |
| 2019/0201089 A1 | 7/2019 | Waldstreicher et al. |
| 2019/0201688 A1 | 7/2019 | Olson |
| 2019/0209235 A1 | 7/2019 | Stewart et al. |
| 2019/0223948 A1 | 7/2019 | Stewart et al. |
| 2019/0231421 A1 | 8/2019 | Viswanathan et al. |
| 2019/0231425 A1 | 8/2019 | Waldstreicher et al. |
| 2019/0254735 A1 | 8/2019 | Stewart et al. |
| 2019/0269912 A1 | 9/2019 | Viswanathan et al. |
| 2019/0298442 A1 | 10/2019 | Ogata et al. |
| 2019/0307500 A1 | 10/2019 | Byrd et al. |
| 2019/0343580 A1 | 11/2019 | Nguyen et al. |
| 2019/0350647 A1 | 11/2019 | Ramberg et al. |
| 2019/0350649 A1 | 11/2019 | Sutermeister et al. |
| 2020/0008869 A1 | 1/2020 | Byrd |
| 2020/0008870 A1 | 1/2020 | Gruba et al. |
| 2020/0009378 A1 | 1/2020 | Stewart et al. |
| 2020/0038104 A1 | 2/2020 | Mickelsen |
| 2020/0046423 A1 | 2/2020 | Mswanathan et al. |
| 2020/0093539 A1 | 3/2020 | Long et al. |
| 2020/0129230 A1 | 4/2020 | Forsyth et al. |
| 2022/0071699 A1 | 3/2022 | Viswanathan |
| 2022/0133405 A1 | 5/2022 | Mickelsen |

FOREIGN PATENT DOCUMENTS

| | | |
|---|---|---|
| EP | 1125549 A2 | 8/2001 |
| EP | 0797956 B1 | 6/2003 |
| EP | 1340469 A1 | 9/2003 |
| EP | 1127552 B1 | 6/2006 |
| EP | 1803411 A2 | 7/2007 |
| EP | 1009303 B1 | 6/2009 |
| EP | 2213729 A2 | 8/2010 |
| EP | 2382935 A1 | 11/2011 |
| EP | 2425871 A2 | 3/2012 |
| EP | 2532320 A2 | 12/2012 |
| EP | 2587275 A1 | 5/2013 |
| EP | 2663227 A1 | 11/2013 |
| EP | 1909678 B1 | 1/2014 |
| EP | 2217165 B1 | 3/2014 |
| EP | 2376193 B1 | 3/2014 |
| EP | 2708181 A1 | 3/2014 |
| EP | 2777579 A1 | 9/2014 |
| EP | 2777585 A1 | 9/2014 |
| EP | 2934307 A1 | 10/2015 |
| EP | 3056242 A1 | 8/2016 |
| EP | 3111871 A1 | 1/2017 |
| EP | 3151773 B1 | 4/2018 |
| JP | 2000-508196 A | 7/2000 |
| JP | 2005-516666 A | 6/2005 |
| JP | 2006-506184 A | 2/2006 |
| JP | 2008-538997 A | 11/2008 |
| JP | 2009-500129 A | 1/2009 |
| JP | 2011-509158 A | 3/2011 |
| JP | 2012-050538 A | 3/2012 |
| JP | 2013-525016 A | 6/2013 |
| JP | 2014-113493 A | 6/2014 |
| JP | 2017-504404 A | 2/2017 |
| JP | 2018-509227 A | 4/2018 |
| JP | 2020-517355 A | 6/2020 |
| WO | 92/07622 A1 | 5/1992 |
| WO | 92/21278 A1 | 12/1992 |
| WO | 92/21285 A1 | 12/1992 |
| WO | 94/07413 A1 | 4/1994 |
| WO | 97/24073 A1 | 7/1997 |

(56) References Cited

FOREIGN PATENT DOCUMENTS

| | | |
|---|---|---|
| WO | 97/25917 A1 | 7/1997 |
| WO | 97/37719 A1 | 10/1997 |
| WO | 99/04851 A1 | 2/1999 |
| WO | 99/22659 A1 | 5/1999 |
| WO | 99/56650 A1 | 11/1999 |
| WO | 99/59486 A2 | 11/1999 |
| WO | 02/56782 A2 | 7/2002 |
| WO | 03/53289 A1 | 7/2003 |
| WO | 03/65916 A1 | 8/2003 |
| WO | 2004/045442 A1 | 6/2004 |
| WO | 2004/086994 A1 | 10/2004 |
| WO | 2005/046487 A1 | 5/2005 |
| WO | 2006/115902 A2 | 11/2006 |
| WO | 2007/006055 A2 | 1/2007 |
| WO | 2007/079438 A2 | 7/2007 |
| WO | 2009/082710 A1 | 7/2009 |
| WO | 2009/089343 A1 | 7/2009 |
| WO | 2009/137800 A2 | 11/2009 |
| WO | 2010/014480 A1 | 2/2010 |
| WO | 2010/056771 A1 | 5/2010 |
| WO | 2011/028310 A1 | 3/2011 |
| WO | 2011/139589 A2 | 11/2011 |
| WO | 2011/154805 A1 | 12/2011 |
| WO | 2012/051433 A2 | 4/2012 |
| WO | 2012/097067 A1 | 7/2012 |
| WO | 2012/153928 A2 | 11/2012 |
| WO | 2013/019385 A1 | 2/2013 |
| WO | 2014/025394 A1 | 2/2014 |
| WO | 2014/031800 A1 | 2/2014 |
| WO | 2014/036439 A2 | 3/2014 |
| WO | 2014/100579 A1 | 6/2014 |
| WO | 2014/160832 A2 | 10/2014 |
| WO | 2015/066322 A1 | 5/2015 |
| WO | 2015/099786 A1 | 7/2015 |
| WO | 2015/100451 A1 | 7/2015 |
| WO | 2015/103530 A1 | 7/2015 |
| WO | 2015/103574 A1 | 7/2015 |
| WO | 2015/130824 A1 | 9/2015 |
| WO | 2015/140741 A1 | 9/2015 |
| WO | 2015/143327 A1 | 9/2015 |
| WO | 2015/171921 A2 | 11/2015 |
| WO | 2015/175944 A1 | 11/2015 |
| WO | 2015/192018 A1 | 12/2015 |
| WO | 2015/192027 A1 | 12/2015 |
| WO | 2016/059027 A1 | 4/2016 |
| WO | 2016/060983 A1 | 4/2016 |
| WO | 2016/081650 A1 | 5/2016 |
| WO | 2016/090175 A1 | 6/2016 |
| WO | 2017/093926 A1 | 6/2017 |
| WO | 2017/119934 A1 | 7/2017 |
| WO | 2017/120169 A1 | 7/2017 |
| WO | 2017/192477 A1 | 11/2017 |
| WO | 2017/192495 A1 | 11/2017 |
| WO | 2017/201504 A1 | 11/2017 |
| WO | 2017/218734 A1 | 12/2017 |
| WO | 2018/005511 A1 | 1/2018 |
| WO | 2018/106569 A1 | 6/2018 |
| WO | 2018/200800 A1 | 11/2018 |
| WO | 2019/023259 A2 | 1/2019 |
| WO | 2019/023280 A1 | 1/2019 |
| WO | 2019/035071 A1 | 2/2019 |
| WO | 2019/133606 A1 | 7/2019 |
| WO | 2019/133608 A1 | 7/2019 |
| WO | 2019/136218 A1 | 7/2019 |
| WO | 2019/143960 A1 | 7/2019 |
| WO | 2019/181612 A1 | 9/2019 |
| WO | 2019/234133 A1 | 12/2019 |

OTHER PUBLICATIONS

Hobbs, E. P., "Investor Relations Update: Tissue Ablation via Irreversible Electroporation (IRE)," Powerpoint (2004), 16 pages.

International Search Report and Written Opinion received for PCT Patent Application No. PCT/US2021/042775, mailed on Nov. 4, 2021, 12 pages.

Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].

Madhavan, M. et al., "Novel Percutaneous Epicardial Autonomic Modulation in the Canine for Atrial Fibrillation: Results of an Efficacy and Safety Study," Pace, 00:1-11 (2016).

Neven, K. et al., "Epicardial linear electroporation ablation and lesion size," Heart Rhythm, 11:1465-1470 (2014).

Neven, K. et al., "Myocardial Lesion Size After Epicardial Electroporation Catheter Ablation After Subxiphoid Puncture," Circ Arrhythm Electrophysiol., 7(4):728-733 (2014).

Neven, K. et al., "Safety and Feasibility of Closed Chest Epicardial Catheter Ablation Using Electroporation," Circ Arrhythm Electrophysiol., 7:913-919 (2014).

Van Driel, V.J.H.M. et al., "Low vulnerability of the right phrenic nerve to electroporation ablation," Heart Rhythm, 12:1838-1844 (2015).

Van Driel, V.J.H.M. et al., "Pulmonary Vein Stenosis After Catheter Ablation Electroporation Versus Radiofrequency," Circ Arrhythm Electrophysiol., 7(4):734-738 (2014).

Wittkampf, F.H. et al., "Feasibility of Electroporation for the Creation of Pulmonary Vein Ostial Lesions," J Cardiovasc Electrophysiol, 22(3):302-309 (Mar. 2011).

Wittkampf, F.H. et al., "Myocardial Lesion Depth With Circular Electroporation Ablation," Circ. Arrhythm Electrophysiol., 5(3):581-586 (2012).

Office Action received for Japanese Patent Application No. 2023-504655, mailed on Nov. 21, 2023, 14 pages (8 pages of English Translation and 6 pages of Original Document).

* cited by examiner

HYBRID ELECTROPORATION ABLATION CATHETER

CROSS REFERENCE TO RELATED APPLICATION

This application claims priority to Provisional Application No. 63/056,300, filed Jul. 24, 2020, which is herein incorporated by reference in its entirety.

TECHNICAL FIELD

The present disclosure relates to medical systems and methods for ablating tissue in a patient. More specifically, the present disclosure relates to medical systems and methods for ablation of tissue by electroporation.

BACKGROUND

Ablation procedures are used to treat many different conditions in patients. Ablation can be used to treat cardiac arrhythmias, benign tumors, cancerous tumors, and to control bleeding during surgery. Usually, ablation is accomplished through thermal ablation techniques including radiofrequency (RF) ablation and cryoablation. In RF ablation, a probe is inserted into the patient and radio frequency waves are transmitted through the probe to the surrounding tissue. The radio frequency waves generate heat, which destroys surrounding tissue and cauterizes blood vessels. In cryoablation, a hollow needle or cryoprobe is inserted into the patient and cold, thermally conductive fluid is circulated through the probe to freeze and kill the surrounding tissue. RF ablation and cryoablation techniques indiscriminately kill tissue through cell necrosis, which may damage or kill otherwise healthy tissue, such as tissue in the esophagus, phrenic nerve cells, and tissue in the coronary arteries.

Another ablation technique uses electroporation. In electroporation, or electro-permeabilization, an electrical field is applied to cells in order to increase the permeability of the cell membrane. The electroporation can be reversible or irreversible, depending on the strength of the electric field. If the electroporation is reversible, the increased permeability of the cell membrane can be used to introduce chemicals, drugs, and/or deoxyribonucleic acid (DNA) into the cell, prior to the cell healing and recovering. If the electroporation is irreversible, the affected cells are killed through apoptosis.

Irreversible electroporation can be used as a nonthermal ablation technique. In irreversible electroporation, trains of short, high voltage pulses are used to generate electric fields that are strong enough to kill cells through apoptosis. In ablation of cardiac tissue, irreversible electroporation can be a safe and effective alternative to the indiscriminate killing of thermal ablation techniques, such as RF ablation and cryoablation. Irreversible electroporation can be used to kill targeted tissue, such as myocardium tissue, by using an electric field strength and duration that kills the targeted tissue but does not permanently damage other cells or tissue, such as non-targeted myocardium tissue, red blood cells, vascular smooth muscle tissue, endothelium tissue, and nerve cells.

SUMMARY

As recited in examples, Example 1 is a hybrid electroporation ablation catheter. The hybrid electroporation ablation catheter comprises a catheter shaft having a proximal end and an opposite distal end and an electrode assembly extending from the distal end of the catheter shaft, the electrode assembly comprising a plurality of energy-delivering electrodes. The electrode assembly is configured to be selectively operable in a first operation mode and a second operation mode. The electrode assembly comprises an inner shaft adapted to be extended from and retracted into the catheter shaft. The plurality of energy-delivering electrodes comprise a plurality of first electrodes and a plurality of second electrodes. When operating in the first operation mode, the inner shaft is extended from the catheter shaft, and the plurality of first electrodes and the plurality of second electrodes are activated. When operating in the second operation mode, the inner shaft is at least partially retracted into the catheter shaft, the plurality of first electrodes are activated, and the plurality of second electrodes are deactivated.

Example 2 is the hybrid electroporation ablation catheter of Example 1, wherein in the first operation mode the electrode assembly is configured to deliver ablative energy to form circumferential ablation lesion having a diameter of between twenty millimeters and twenty-eight millimeters, and wherein in the second operation mode the electrode assembly is configured to deliver ablative energy to form a focal ablation lesion having a diameter of between five millimeters and twenty millimeters Example 3 is the hybrid electroporation ablation catheter of Example 1, wherein the electrode assembly further comprises a plurality of splines connected to the inner shaft at a distal end of the inner shaft, wherein the plurality of energy-delivering electrodes are disposed on the plurality of splines.

Example 4 is the hybrid electroporation ablation catheter of Example 3, wherein the plurality of splines form a first cavity having a first diameter in the first operation mode, wherein the plurality of splines form a second cavity having a second diameter in the second operation mode, and wherein the first diameter is larger than the second diameter.

Example 5 is the hybrid electroporation ablation catheter of Example 1, wherein the plurality of second electrodes are disposed closer to a distal end of the inner shaft than the plurality of first electrodes.

Example 6 is the hybrid electroporation ablation catheter of any one of Examples 1-5, wherein the catheter shaft is deflectable.

Example 7 is the hybrid electroporation ablation catheter of any one of Examples 1-6, wherein the plurality of second electrodes are retracted into the catheter shaft in the second operation mode.

Example 8 is the hybrid electroporation ablation catheter of Example 1, further comprising: one or more return electrodes disposed on the catheter shaft.

Example 9 is the hybrid electroporation ablation catheter of any one of Examples 1-8, further comprising: an actuator configured to move the inner shaft relative to the catheter shaft, and a sensor configured to detect a position of the actuator.

Example 10 is the hybrid electroporation ablation catheter of Example 9, wherein the hybrid electroporation ablation catheter is configured to set to one of the first operation mode and the second operation mode based on the detected position of the actuator.

Example 11 is the hybrid electroporation ablation catheter of Example 1, wherein the plurality of first electrodes is individually controllable.

Example 12 is the hybrid electroporation ablation catheter of Example 1, wherein the plurality of second electrodes is individually controllable.

Example 13 is a system comprising any one of the hybrid electroporation ablation catheter of Examples 1-12.

Example 14 is the system of Example 13, further comprising: a pulse generator configured to generate and deliver electroporation pulse to the hybrid electroporation ablation device.

Example 15 is the system of Example 14, further comprising: a controller coupled to the pulse generator and the hybrid electroporation ablation device and configured to select an operation mode of the hybrid electroporation ablation device.

Example 16 is a hybrid electroporation ablation catheter. The hybrid electroporation ablation catheter comprises a catheter shaft having a proximal end and an opposite distal end and an electrode assembly extending from the distal end of the catheter shaft, the electrode assembly comprising a plurality of energy-delivering electrodes. The electrode assembly is configured to be selectively operable in a first operation mode and a second operation mode. The electrode assembly comprises an inner shaft adapted to be extended from and retracted into the catheter shaft. The plurality of energy-delivering electrodes comprise a plurality of first electrodes and a plurality of second electrodes. When operating in the first operation mode, the inner shaft is extended from the catheter shaft, and the plurality of first electrodes and the plurality of second electrodes are activated. When operating in the second operation mode, the inner shaft is at least partially retracted into the catheter shaft, the plurality of first electrodes are activated, and the plurality of second electrodes are deactivated.

Example 17 is the hybrid electroporation ablation catheter of Example 16, wherein in the first operation mode the electrode assembly is configured to deliver ablative energy to form circumferential ablation lesion having a diameter of between twenty millimeters and twenty-eight millimeters, and wherein in the second operation mode the electrode assembly is configured to deliver ablative energy to form a focal ablation lesion having a diameter of between five millimeters and twenty millimeters Example 18 is the hybrid electroporation ablation catheter of Example 16, wherein the electrode assembly further comprises a plurality of splines connected to the inner shaft at a distal end of the inner shaft, wherein the plurality of energy-delivering electrodes are disposed on the plurality of splines.

Example 19 is the hybrid electroporation ablation catheter of Example 18, wherein the plurality of splines form a first cavity having a first diameter in the first operation mode, wherein the plurality of splines form a second cavity having a second diameter in the second operation mode, and wherein the first diameter is larger than the second diameter.

Example 20 is the hybrid electroporation ablation catheter of Example 16, wherein the plurality of second electrodes are disposed closer to a distal end of the inner shaft than the plurality of first electrodes.

Example 21 is the hybrid electroporation ablation catheter of Example 16, wherein the catheter shaft is deflectable.

Example 22 is the hybrid electroporation ablation catheter of Example 16, wherein the plurality of second electrodes are retracted into the catheter shaft in the second operation mode.

Example 23 is the hybrid electroporation ablation catheter of Example 16, further comprising: one or more return electrodes disposed on the catheter shaft.

Example 24 is the hybrid electroporation ablation catheter of Example 16, further comprising: an actuator configured to move the inner shaft relative to the catheter shaft, and a sensor configured to detect a position of the actuator.

Example 25 is the hybrid electroporation ablation catheter of Example 24, wherein the hybrid electroporation ablation catheter is configured to set to one of the first operation mode and the second operation mode based on the detected position of the actuator.

Example 26 is the hybrid electroporation ablation catheter of Example 16, wherein the plurality of first electrodes is individually controllable.

Example 27 is the hybrid electroporation ablation catheter of Example 16, wherein the plurality of second electrodes is individually controllable.

Example 28 is a hybrid electroporation ablation system. The hybrid electroporation ablation system comprises a hybrid electroporation ablation catheter, a pulse generator configured to generate and deliver electroporation pulse to the hybrid electroporation ablation device, and a controller coupled to the pulse generator and the electroporation ablation device. The hybrid electroporation ablation catheter comprises a catheter shaft having a proximal end and an opposite distal end and an electrode assembly extending from the distal end of the catheter shaft, the electrode assembly comprising a plurality of energy-delivering electrodes. The electrode assembly is configured to be selectively operable in a first operation mode and a second operation mode. The electrode assembly comprises an inner shaft adapted to be extended from and retracted into the catheter shaft. The plurality of energy-delivering electrodes comprise a plurality of first electrodes and a plurality of second electrodes. When operating in the first operation mode, the inner shaft is extended from the catheter shaft, and the plurality of first electrodes and the plurality of second electrodes are activated. When operating in the second operation mode, the inner shaft is at least partially retracted into the catheter shaft, the plurality of first electrodes are activated, and the plurality of second electrodes are deactivated.

Example 29 is the hybrid electroporation ablation system of Example 28, wherein in the first operation mode the electrode assembly is configured to deliver ablative energy to form circumferential ablation lesion having a diameter of between twenty millimeters and twenty-eight millimeters, and wherein in the second operation mode the electrode assembly is configured to deliver ablative energy to form a focal ablation lesion having a diameter of between five millimeters and twenty millimeters Example 30 is the hybrid electroporation ablation system of Example 28, wherein the electrode assembly further comprises a plurality of splines connected to the inner shaft at a distal end of the inner shaft, wherein the plurality of energy-delivering electrodes are disposed on the plurality of splines.

Example 31 is the hybrid electroporation ablation system of Example 28, wherein the controller is configured to select an operation mode of the hybrid electroporation ablation device.

Example 32 is a method for electroporation ablations. The method includes the steps of: deploying a hybrid electroporation ablation catheter approximate to a target tissue, the hybrid electroporation ablation catheter operable in a plurality of operation modes, the plurality of operation modes comprising a first operation mode and a second operation mode, the hybrid electroporation ablation catheter configured to deliver ablative energy to form circumferential ablation lesion in the first operation mode and configured to deliver ablative energy to form a focal ablation lesion in the second operation mode; selecting an operation mode from the plurality of operation modes of the hybrid electroporation ablation catheter; operating the hybrid electroporation ablation catheter in the selected operation mode; and generating an electric field at a plurality of electrodes of the catheter according to the selected operation mode, the electric field having an electric field strength sufficient for ablating target tissue via irreversible electroporation.

Example 33 is the method of Example 32, wherein the hybrid electroporation ablation catheter comprises a catheter shaft and an electrode assembly extending from a distal end of the catheter shaft.

Example 34 is the method of Example 33, wherein the electrode assembly comprises a plurality of electrodes, and wherein at least one of the plurality of electrodes is deactivated in one of the plurality of operation modes.

Example 35 is the method of Example 32, wherein the electrode assembly is configured to form a plurality of shapes in the plurality of operation modes, and wherein the plurality of shapes have a different volume from each other.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
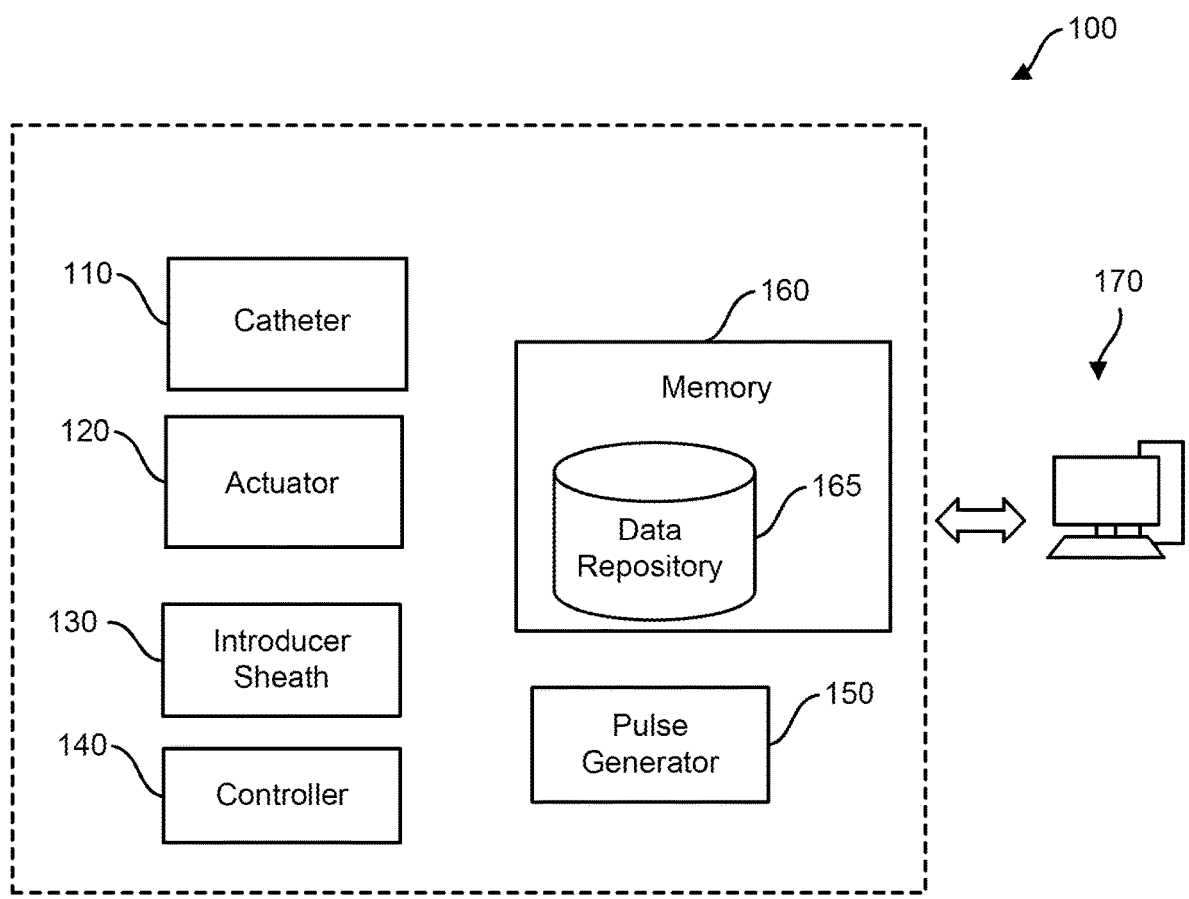
FIG. 1 depicts an illustrative system diagram for an electroporation ablation system or device, in accordance with embodiments of the subject matter of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although illustrative methods may be represented by one or more drawings (e.g., flow diagrams, communication flows, etc.), the drawings should not be interpreted as implying any requirement of, or particular order among or between, various steps disclosed herein. However, certain some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

Cryo energy and radio-frequency (RF) energy kill tissues indiscriminately through cell necrosis, which can damage the esophagus, the phrenic nerve, coronary arteries, in addition to other undesired effects. Irreversible electroporation (IRE) uses high voltage, short (e.g., 100 microseconds or shorter) pulses to kill cells through apoptosis. IRE can be targeted to kill myocardium, sparing other adjacent tissues including the esophageal vascular smooth muscle and endothelium.

The present disclosure describes devices and methods for implementing multiple ablation strategies, i.e., circumferential ablation and focal ablation, using a single IRE ablation catheter. Circumferential ablation involves forming substantially circular, ring-shaped ablation lesions of relatively large diameter, and is particularly useful for ablating the pulmonary vein ostia in so-called "pulmonary vein isolation" (PVI) procedures for treating paroxysmal AF. This requires an IRE ablation catheter with an electrode set having a relatively larger footprint to treat the pulmonary vein ostia, ideally with a single energy application. Focal ablation, in contrast, creates lesions that are significantly smaller than circumferential lesions formed in PVI procedures, and is generally employed to create lines of electrical block using sequential energy applications, e.g., along the cardiac chamber wall, to treat atrial tachycardias, AV reentrant arrhythmias, persistent AF, and the like. Focal ablation via IRE requires an IRE ablation catheter with electrode sets arranged in a smaller footprint as compared to the aforementioned catheters for forming circumferential lesions. Currently, circumferential ablation and focal ablation require catheters specifically designed for each ablation strategy, which in turn require removal of one ablation catheter, e.g., the circumferential ablation catheter following PVI, and replacement with a focal ablation catheter if both circumferential and focal ablation strategies are warranted in a single clinical procedure.

Embodiments of the present disclosure are directed to systems/devices and methods for IRE that are capable of implementing two or more ablation strategies (e.g., circumferential and focal ablation) using a single catheter, referred to as hybrid electroporation ablation catheter. In some embodiments, a hybrid exploration ablation catheter is configured to have two operation modes, with one suitable for circumferential ablation and one suitable for focal ablation. In some cases, the hybrid catheter in different operation modes has different shapes of the electrode assembly. In some cases, the hybrid catheter in different operation modes has different sets of electrodes being activated in the electrode assembly. In some cases, the hybrid catheter in different operation modes has both different sets of electrodes being activated and different shapes in the electrode assembly. In some embodiments, the two or more operation modes can be selected by an operator depending on the intended ablation strategy. In some embodiments, the two or more operation modes can be selected by a controller automatically depending on the intended ablation strategy and/or sensing data.

FIG. 1 depicts an illustrative system diagram for an electroporation ablation system or device 100, in accordance with embodiments of the subject matter of the disclosure. The electroporation ablation system/device 100 includes one or more hybrid electroporation ablation catheters 110, an introducer sheath 130, a controller 140, a pulse generator 150, and a memory 160. In embodiments, the electroporation ablation system/device 100 is configured to deliver electric field energy to target tissue in a patient's heart to create tissue apoptosis, rendering the tissue incapable of conducting electrical signals. In some cases, the electroporation ablation system/device 100 may connect with other system(s) 170, for example, a mapping system, an electrophysiology system, and/or the like.

In embodiments, the hybrid electroporation ablation catheter 110 is designed to have two or more operation modes, each operation mode is suitable for a type of ablation operation (e.g., circumferential or single shot ablation, focal ablation, segment ablation, etc.). The catheter 110 is designed to be disposed by a target ablation location in the intracardiac chamber. As used herein, an intracardiac chamber refers to cardiac chamber and its surrounding blood vessels (e.g., pulmonary veins). The pulse generator 150 is configured to generate ablative pulse/energy, or referred to as electroporation pulse/energy, to be delivered to electrodes of the catheter 110. The electroporation pulse is typically high voltage and short pulse. The electroporation controller 140 is configured to control functional aspects of the electroporation ablation system/device 100. In embodiments, the electroporation controller 140 is configured to control the pulse generator 150 on the generation and delivery of ablative energy to electrodes of the catheter 110. In embodiments, the controller 140 is configured to control the operation mode of the hybrid electroporation ablation catheter 110.

In one embodiment, the catheter 110 has one or more electrodes. In some embodiments, the catheter 110 includes an electrode assembly including one or more electrodes. In some cases, the electrode assembly is configured to deliver different electric field energies in magnitude in different operation modes. In some cases, the electrode assembly includes an expandable component that is configured to have different expanded shapes in different operation modes. In some cases, the operation modes are varied with the shapes and/or diameter of the electrode assembly. In some cases, each of the one or more electrodes of the catheter 110 is individually addressable and controllable. In some cases, the controller 140 may control the ablative energy delivery to each electrode, such that the electric field formed by the plurality of electrodes can be controlled and adjusted. In some cases, a part of the one or more electrodes can be deactivated by the controller 140.

In some cases, a specific set of electrodes can be activated by the controller 140 for an operation mode. In some cases, a part of the one or more electrodes can be retracted into a shaft of the catheter 110 in a specific operation mode. In some cases, a distance between adjacent active electrodes is generally the same among all active electrodes or a subset of active electrodes. In one example, the electrodes are active every other ones in an operation mode, for example, when the electrode assembly has a relatively small operation diameter. In one embodiment, a distance between adjacent active electrodes is generally the same (e.g., within 10% variation from the average distance) at a first operation (e.g., circumferential ablation) as at a second distance (e.g., focal ablation), while other electrodes are deactivated.

In some cases, the electroporation controller 140 receives sensor data collected by sensor(s) of catheter(s). In some cases, the electroporation controller 140 can change the operation mode of the catheter 110 in response to the receiving sensing data. In some cases, the electroporation system/device 100 may include an actuator 120 configured to change the operational shape of the electrode assembly of the catheter 110. In some cases, the electroporation system/device 100 may further include a position sensor to monitor the position of the actuator. In one example, the controller 140 can receive sensing data generated by the position sensor and change the operation mode of the catheter in response to the position of the actuator. In embodiments, the actuator 120 is integrated with or connected to the catheter 110.

In some cases, the electroporation controller 140 can change the ablative energy delivered to electrodes in response to the sensing data. In some cases, the electroporation controller 140 is configured to model the electric fields that can be generated by the catheter 110, which often includes consideration of the physical characteristics of the electroporation ablation catheter 110 including the electrodes and spatial relationships of the electrodes on the electroporation ablation catheter 110. In embodiments, the electroporation controller 140 is configured to control the electric field strength of the electric field formed by the electrodes of the catheter 110 to be no higher than 1500 volts per centimeter.

In embodiments, the electroporation controller 140 includes one or more controllers, microprocessors, and/or computers that execute code out of memory 160, for example, non-transitory machine readable medium, to control and/or perform the functional aspects of the electroporation ablation system/device 100. In embodiments, the memory 160 can be part of the one or more controllers, microprocessors, and/or computers, and/or part of memory capacity accessible through a network, such as the world wide web. In embodiments, the memory 160 comprises a data repository 165, which is configured to store ablation data (e.g., location, energy, etc.), sensed data, modelled electric field data, treatment plan data, and/or the like.

In embodiments, the introducer sheath 130 is operable to provide a delivery conduit through which the hybrid electroporation ablation catheter 110 can be deployed to specific target sites within a patient's cardiac chamber.

In embodiments, the other systems 170 includes an electro-anatomical mapping (EAM) system. In some cases, the EAM system is operable to track the location of the various functional components of the electroporation ablation system/device 100, and to generate high-fidelity three-dimensional anatomical and electro-anatomical maps of the cardiac chambers of interest. In embodiments, the EAM system can be the RHYTHMIA™ HDx mapping system marketed by Boston Scientific Corporation. Also, in embodiments, the mapping and navigation controller of the EAM system includes one or more controllers, microprocessors, and/or computers that execute code out of memory to control and/or perform functional aspects of the EAM system.

The EAM system generates a localization field, via a field generator, to define a localization volume about the heart, and one or more location sensors or sensing elements on the tracked device(s), e.g., the electroporation ablation catheter pair 105, generate an output that can be processed by a mapping and navigation controller to track the location of the sensor, and consequently, the corresponding device, within the localization volume. In one embodiment, the device tracking is accomplished using magnetic tracking techniques, whereby the field generator is a magnetic field generator that generates a magnetic field defining the localization volume, and the location sensors on the tracked devices are magnetic field sensors.

In some embodiments, impedance tracking methodologies may be employed to track the locations of the various devices. In such embodiments, the localization field is an electric field generated, for example, by an external field generator arrangement, e.g., surface electrodes, by intrabody or intra-cardiac devices, e.g., an intracardiac catheter, or both. In these embodiments, the location sensing elements can constitute electrodes on the tracked devices that generate outputs received and processed by the mapping and navigation controller to track the location of the various location sensing electrodes within the localization volume.

In embodiments, the EAM system is equipped for both magnetic and impedance tracking capabilities. In such embodiments, impedance tracking accuracy can, in some instances be enhanced by first creating a map of the electric field induced by the electric field generator within the cardiac chamber of interest using a probe equipped with a magnetic location sensor, as is possible using the aforementioned RHYTHMIA HDx™ mapping system. One exemplary probe is the INTELLAMAP ORION™ mapping catheter marketed by Boston Scientific Corporation.

Regardless of the tracking methodology employed, the EAM system utilizes the location information for the various tracked devices, along with cardiac electrical activity acquired by, for example, the electroporation ablation catheter pair 105 or another catheter or probe equipped with sensing electrodes, to generate, and display via a display, detailed three-dimensional geometric anatomical maps or representations of the cardiac chambers as well as electro-anatomical maps in which cardiac electrical activity of interest is superimposed on the geometric anatomical maps. Furthermore, the EAM system can generate a graphical representation of the various tracked devices within the geometric anatomical map and/or the electro-anatomical map.

According to embodiments, various components (e.g., the controller 140) of the electrophysiology system 100 may be implemented on one or more computing devices. A computing device may include any type of computing device suitable for implementing embodiments of the disclosure. Examples of computing devices include specialized computing devices or general-purpose computing devices such "workstations," "servers," "laptops," "desktops," "tablet computers," "hand-held devices," "general-purpose graphics processing units (GPGPUs)," and the like, all of which are contemplated within the scope of FIG. 1 with reference to various components of the system 100.

In some embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices.

In some embodiments, the memory 160 includes computer-readable media in the form of volatile and/or nonvolatile memory, transitory and/or non-transitory storage media and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the memory 160 stores computer-executable instructions for causing a processor (e.g., the controller 140) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Program components may be programmed using any number of different programming environments, including various languages, development kits, frameworks, and/or the like. Some or all of the functionality contemplated herein may also, or alternatively, be implemented in hardware and/or firmware.

The data repository 165 may be implemented using any one of the configurations described below. A data repository may include random access memories, flat files, XML files, and/or one or more database management systems (DBMS) executing on one or more database servers or a data center. A database management system may be a relational (RDBMS), hierarchical (HDBMS), multidimensional (MDBMS), object oriented (ODBMS or OODBMS) or object relational (ORDBMS) database management system, and the like. The data repository may be, for example, a single relational database. In some cases, the data repository may include a plurality of databases that can exchange and aggregate data by data integration process or software application. In an exemplary embodiment, at least part of the data repository 165 may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Various components of the system/device 100 can communicate via or be coupled to via a communication interface, for example, a wired or wireless interface. The communication interface includes, but not limited to, any wired or wireless short-range and long-range communication interfaces. The wired interface can use cables, umbilicals, and the like. The short-range communication interfaces may be, for example, local area network (LAN), interfaces conforming known communications standard, such as Bluetooth® standard, IEEE 802 standards (e.g., IEEE 802.11), a ZigBee® or similar specification, such as those based on the IEEE 802.15.4 standard, or other public or proprietary wireless protocol. The long-range communication interfaces may be, for example, wide area network (WAN), cellular network interfaces, satellite communication interfaces, etc. The communication interface may be either within a private computer network, such as intranet, or on a public computer network, such as the internet.

Figure 2A:
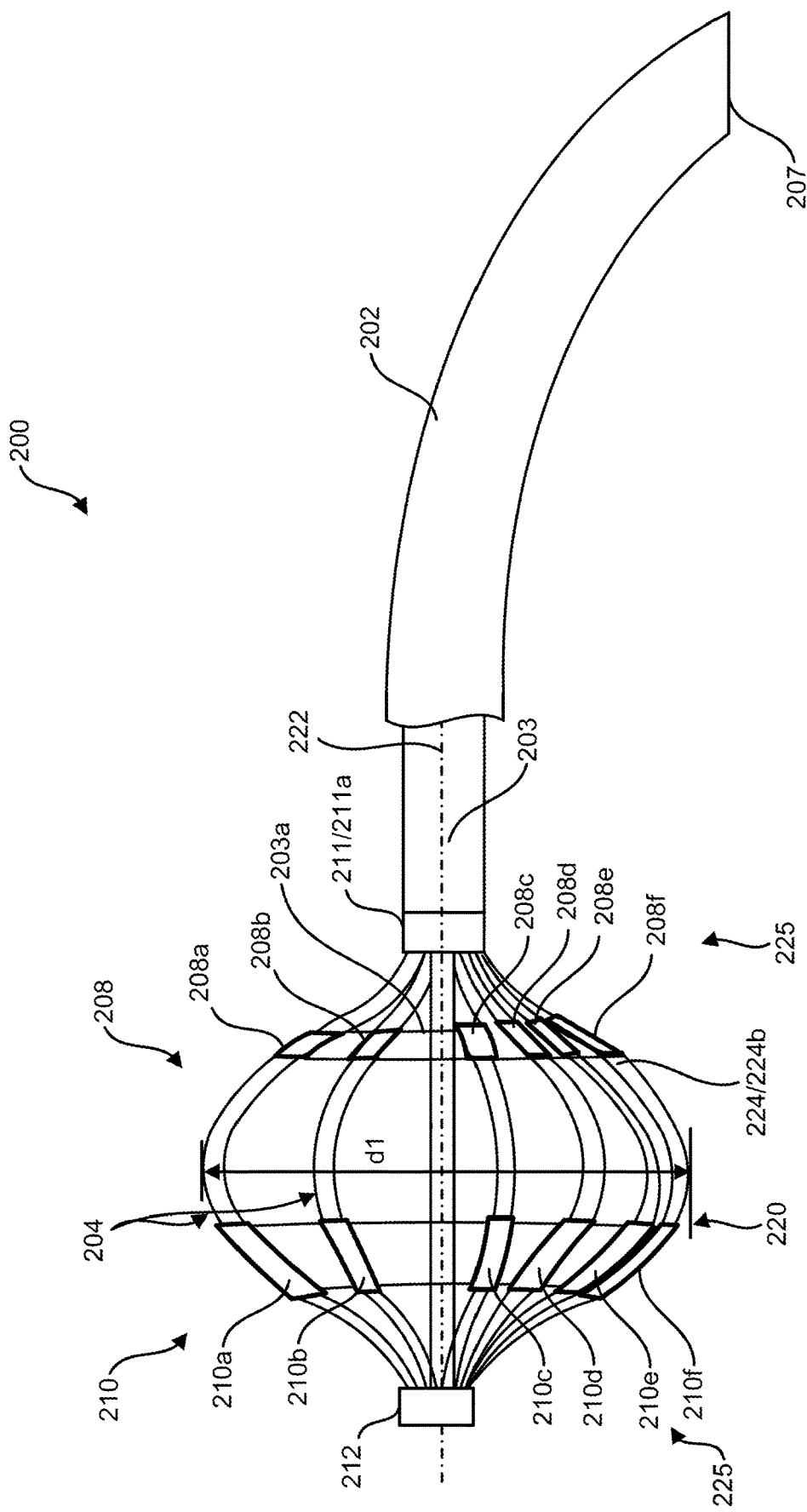
FIG. 2A is a diagram illustrating a hybrid electroporation ablation catheter in a first operation mode, in accordance with embodiments of the subject matter of the disclosure.
Figure 2B:
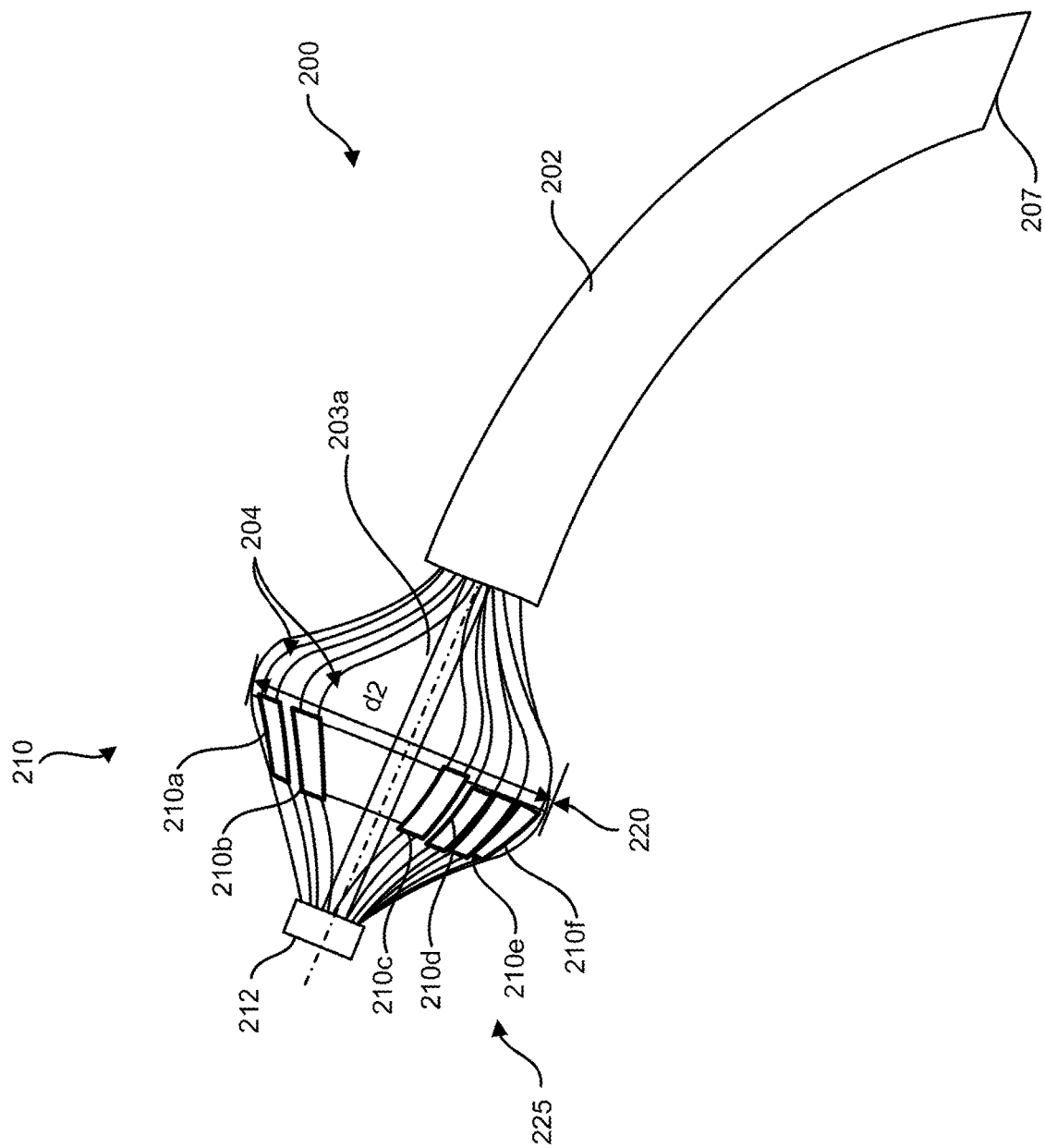
FIG. 2B is a diagram illustrating the hybrid electroporation ablation catheter illustrated in FIG. 2A in a second operation mode, in accordance with embodiments of the subject matter of the disclosure.

FIG. 2A is a diagram illustrating a portion of a hybrid electroporation ablation catheter 200 in a first operation mode; FIG. 2B is a diagram illustrating the hybrid electroporation ablation catheter 200 in a second operation mode, in accordance with embodiments of the subject matter of the disclosure. As shown, the catheter 200 includes a catheter shaft 202 and an inner shaft 203 disposed within the catheter shaft 202, and extending distally from a distal end 206 of the catheter shaft 202. As will be appreciated, the catheter shaft 202 is coupled, at its proximal end, to a handle assembly (not shown) configured to be manipulated by a user during an electroporation ablation procedure. As further shown, the catheter 200 includes an electrode assembly 220 at a distal end extending from the distal end 206 of the catheter shaft 202.

In embodiments, the electrode assembly 220 comprising a plurality of energy-delivering electrodes 225, where the electrode assembly 220 is configured to be selectively operable in a first operation mode and a second operation mode. In some cases, in the first operation mode the electrode assembly is configured to deliver ablative energy to form circumferential ablation lesion having a diameter of between twenty (20) millimeters and twenty-eight (28) millimeters. In some cases, in the first operation mode the electrode assembly is configured to deliver ablative energy to form circumferential ablation lesion having a diameter of between twenty-two (22) millimeters and thirty-five (35) millimeters. In some cases, in the first operation mode the electrode assembly is configured to deliver ablative energy to form circumferential ablation lesion having a diameter of between twenty (20) millimeters and thirty-five (35) millimeters. In some cases, in the second operation mode the electrode assembly is configured to deliver ablative energy to form a focal ablation lesion having a diameter of between five (5) millimeters and twenty (20) millimeters. In some cases, in the second operation mode the electrode assembly is configured to deliver ablative energy to form a focal ablation lesion having a diameter of between two (2) millimeters and sixteen (16) millimeters. In some cases, in the second operation mode the electrode assembly is configured to deliver ablative energy to form a focal ablation lesion having a diameter of between two (2) millimeters and twenty (20) millimeters. In some cases, in the first operation mode the electrode assembly is configured to deliver ablative energy to form circumferential ablation lesion having a depth of three (3) millimeters and four (4) millimeters.

In some embodiments, the electrode assembly 220 includes an inner shaft 203, where the inner shaft 203 is adapted to be extended from and retracted into the catheter shaft 202. In some cases, the electrode assembly 220 includes a plurality of splines 204 connected to the inner shaft 203 at a distal end 211 of the inner shaft 203. In some cases, the electrode assembly 220 further includes a center shaft 203a having a proximal end 211a (overlapped with the distal end 211 of the inner shaft 203) and a distal end 212. In some cases, the plurality of splines 204 are connected to the distal end 212 of the center shaft 203a. In embodiments, the electrodes 225 includes a plurality of first electrodes 208 and a plurality of second electrodes 210 disposed on the plurality of splines 204. In one example, the plurality of second electrodes 210 are disposed close to the distal end 212 of the center shaft 203a and the plurality of first electrodes 208 are disposed close to the proximal end 211a of the center shaft 203a.

In some cases, when operating in the first operation mode, the inner shaft 203 and the center shaft 203a are extended from the catheter shaft 202, for example, as illustrated in FIG. 2A. In some cases, in the first operation mode, both the plurality of first electrodes 208 and the plurality of second electrodes 210 are activated selectively energized to form relatively large diameter, circumferential ablation lesions, e.g., such as are created in a PVI procedure.

In some embodiments, when operating in the second operation mode, the inner shaft 203 and the center shaft 203a are at least partially retracted into the catheter shaft 202 such that all or a part of the plurality of first electrodes 208 are retracted into the catheter shaft 202, for example, as illustrated in FIG. 2B. In some cases, in the second operation mode, the plurality of first electrodes 208 are deactivated (e.g., by electrically disconnecting the first electrodes 208 from any pulse generator circuitry) and the plurality of second electrodes 210 are activated and used to create focal ablation lesions via electroporation.

The hybrid electroporation ablation catheter 200 has a longitudinal axis 222. As used herein, a longitudinal axis refers to a line passing through the centroid of the cross sections of an object. In embodiments, the plurality of splines 204 forms a cavity 224. The plurality of splines 204 forms a cavity 224a in the first operation mode and forms a cavity 224b in the second operation mode. In embodiments, the cavity 224a is larger than the cavity 224b in volume. In some embodiments, in the first operation mode, the largest cross-sectional area generally perpendicular to the longitudinal axis 222 of the cavity 224a has a diameter d1. In some embodiments, in the second operation mode, the largest cross-sectional area generally perpendicular to the longitudinal axis 222 of the cavity 224b has a diameter d2. In some cases, the diameter d1 is larger than the diameter d2. In some examples, the diameter d1 is in the range of twenty (20) millimeters and thirty-five (35) millimeters. In some examples, the diameter d2 is in the range of five (5) millimeters and sixteen (16) millimeters. In one example, the diameter d1 is greater than the diameter d2 by 30% to 100%. In one example, the diameter d1 is greater than the diameter d2 by at least 30%. In one example, the diameter d1 is greater than the diameter d2 by at least 100% (i.e., at least two times of the diameter d2). In one example, the diameter d1 is greater than the diameter d2 by at least 150% (i.e., at least two and a half times of the diameter d2).

Figure 2C:
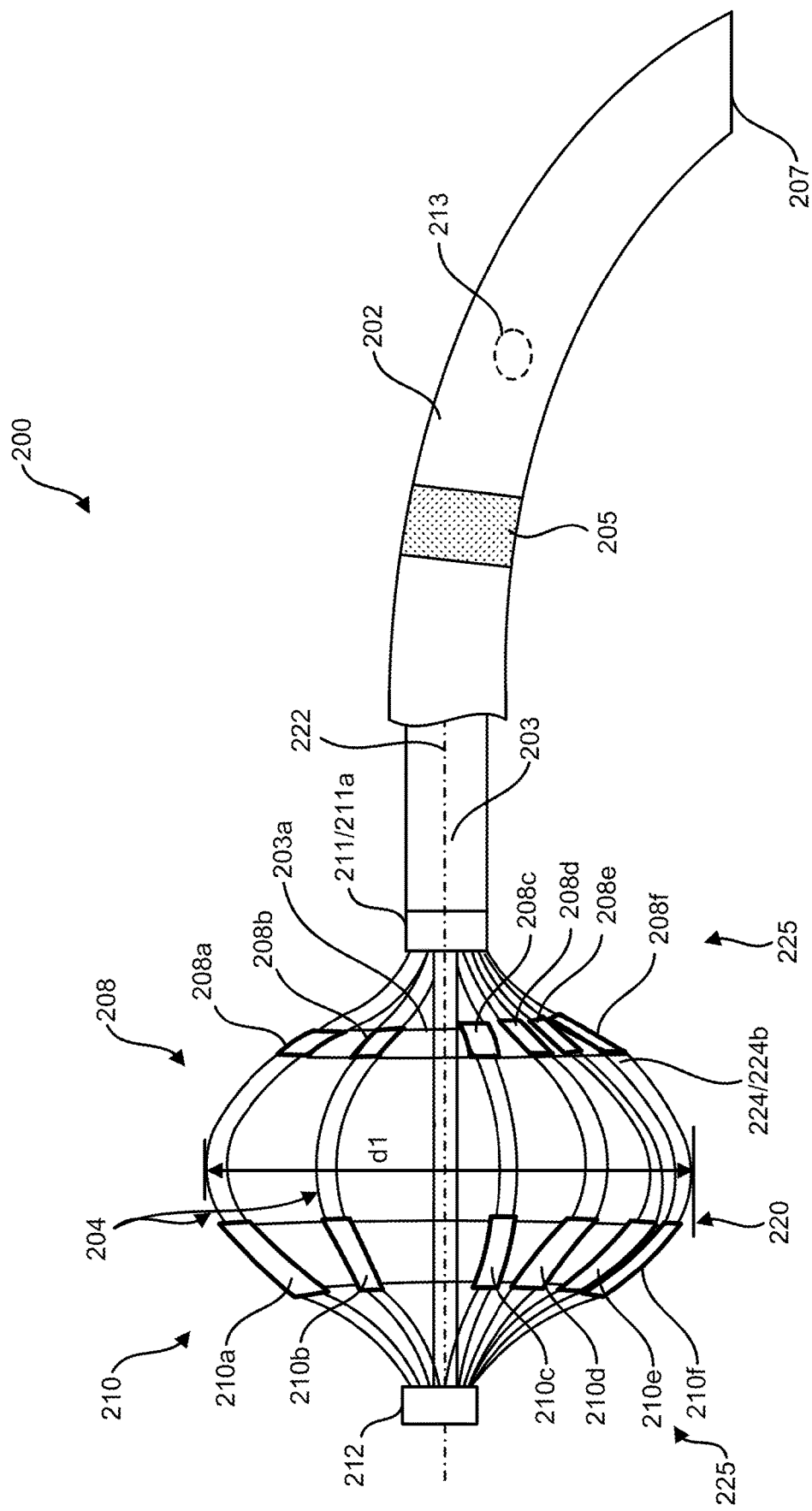
FIG. 2C is a diagram illustrating the hybrid electroporation ablation catheter illustrated in FIG. 2A with additional components, in accordance with embodiments of the subject matter of the disclosure.

In some cases, the catheter shaft 202 is deflectable, implemented using techniques generally known in the art. In some cases, the catheter 200 includes an inflatable balloon (not shown) disposed in the cavity 224 of the splines 204. FIG. 2C is a diagram illustrating the hybrid electroporation ablation catheter illustrated in FIG. 2A with additional features, in accordance with embodiments of the subject matter of the disclosure. In some embodiments, the catheter 200C includes one or more return electrodes 205. In some cases, the one or more return electrodes 205 are disposed on the catheter shaft 202. In some cases, the catheter 200C may include an actuator (not shown) configured to move the inner shaft 203 relative to the catheter shaft 202. In some cases, the actuator is external of the catheter 200C but connected to the catheter 200C. In some cases, the catheter 200 may include a sensor 213 configured to detect a position of the actuator. In one embodiment, the operation mode of the hybrid electroporation ablation catheter 200 is set based on the detected position of the actuator. In one embodiment, the operation mode of the hybrid electroporation ablation catheter 200 is set based on a sensor signal generated by the sensor 213.

In some cases, the first group of electrodes 208 disposed at or proximate the circumference of the plurality of splines 204 and the second group of electrodes 210 disposed proximate to the distal end 212 of the catheter 200. In some cases, the first group of electrodes 208 are referred to as proximal electrodes, and the second group of electrodes 210 are referred to as distal electrodes, where the distal electrodes 210 are disposed closer to the distal end 212 of the electroporation ablation catheter 200 than the proximal electrodes 208. In some implementations, the electrodes 225 can include a thin film of an electro-conductive or optical ink. The ink can be polymer-based. The ink may additionally comprise materials such as carbon and/or graphite in combination with conductive materials. The electrode can include a biocompatible, low resistance metal such as silver, silver flake, gold, and platinum which are additionally radiopaque.

Each of the electrodes in the first group of electrodes 208 and each of the electrodes in the second group of electrodes 210 is configured to conduct electricity and to be operably connected to a controller (e.g., the controller 140 in FIG. 1) and an ablative energy generator (e.g., the pulse generator 150 of FIG. 1). In embodiments, one or more of the electrodes in the first group of electrodes 208 and the second group of electrodes 210 includes flex circuits. In some cases, the plurality of first electrodes 208 are individually controllable. In some cases, the plurality of second electrodes are individually controllable. In some cases, all or a part of the plurality of first electrodes 208 are deactivated in the second operation mode. In some cases, a part of the plurality of second electrodes 210 are deactivated in the second operation mode.

Electrodes in the first group of electrodes 208 are spaced apart from electrodes in the second group of electrodes 210. The first group of electrodes 208 includes electrodes 208a-208f and the second group of electrodes 210 includes electrodes 210a-210f. Also, electrodes in the first group of electrodes 208, such as electrodes 208a-208f, are spaced apart from one another and electrodes in the second of electrodes 210, such as electrodes 210a-210f, are spaced apart from one another.

The spatial relationships and orientation of the electrodes in the first group of electrodes 208 and the spatial relationships and orientation of the electrodes in the second group of electrodes 210 in relation to other electrodes on the same catheter 200 is known or can be determined. In embodiments, the spatial relationships and orientation of the electrodes in the first group of electrodes 208 and the spatial relationships and orientation of the electrodes in the second group of electrodes 210 in relation to other electrodes on the same catheter 200 is constant, once the catheter is deployed.

As to electric fields, in embodiments, each of the electrodes in the first group of electrodes 208 and each of the electrodes in the second group of electrodes 210 can be selected to be an anode or a cathode, such that electric fields can be set up between any two or more of the electrodes in the first and second groups of electrodes 208 and 210. Also, in embodiments, each of the electrodes in the first group of electrodes 208 and each of the electrodes in the second group of electrodes 210 can be selected to be a biphasic pole, such that the electrodes switch or take turns between being an anode and a cathode. Also, in embodiments, groups of the electrodes in the first group of electrodes 208 and groups of the electrodes in the second group of electrodes 210 can be selected to be an anode or a cathode or a biphasic pole, such that electric fields can be set up between any two or more groups of the electrodes in the first and second groups of electrodes 208 and 210.

In embodiments, electrodes in the first group of electrodes 208 and the second group of electrodes 210 can be selected to be biphasic pole electrodes, such that during a pulse train including a biphasic pulse train, the selected electrodes switch or take turns between being an anode and a cathode, and the electrodes are not relegated to monophasic delivery where one is always an anode and another is always a cathode. In some cases, the electrodes in the first and second group of electrodes 208 and 210 can form electric fields with electrode(s) of another catheter. In such cases, the electrodes in the first and second group of electrodes 208 and 210 can be anodes of the fields, or cathodes of the fields.

Further, as described herein, the electrodes are selected to be one of an anode and a cathode, however, it is to be understood without stating it that throughout the present disclosure the electrodes can be selected to be biphasic poles, such that they switch or take turns between being anodes and cathodes. In some cases, one or more of the electrodes in the first group of electrodes 208 are selected to be cathodes and one or more of the electrodes in the second group of electrodes 210 are selected to be anodes. In embodiments, one or more of the electrodes in the first group of electrodes 208 can be selected as a cathode and another one or more of the electrodes in the first group of electrodes 208 can be selected as an anode. In addition, in embodiments, one or more of the electrodes in the second group of electrodes 210 can be selected as a cathode and another one or more of the electrodes in the second group of electrodes 210 can be selected as an anode.

Figure 3:
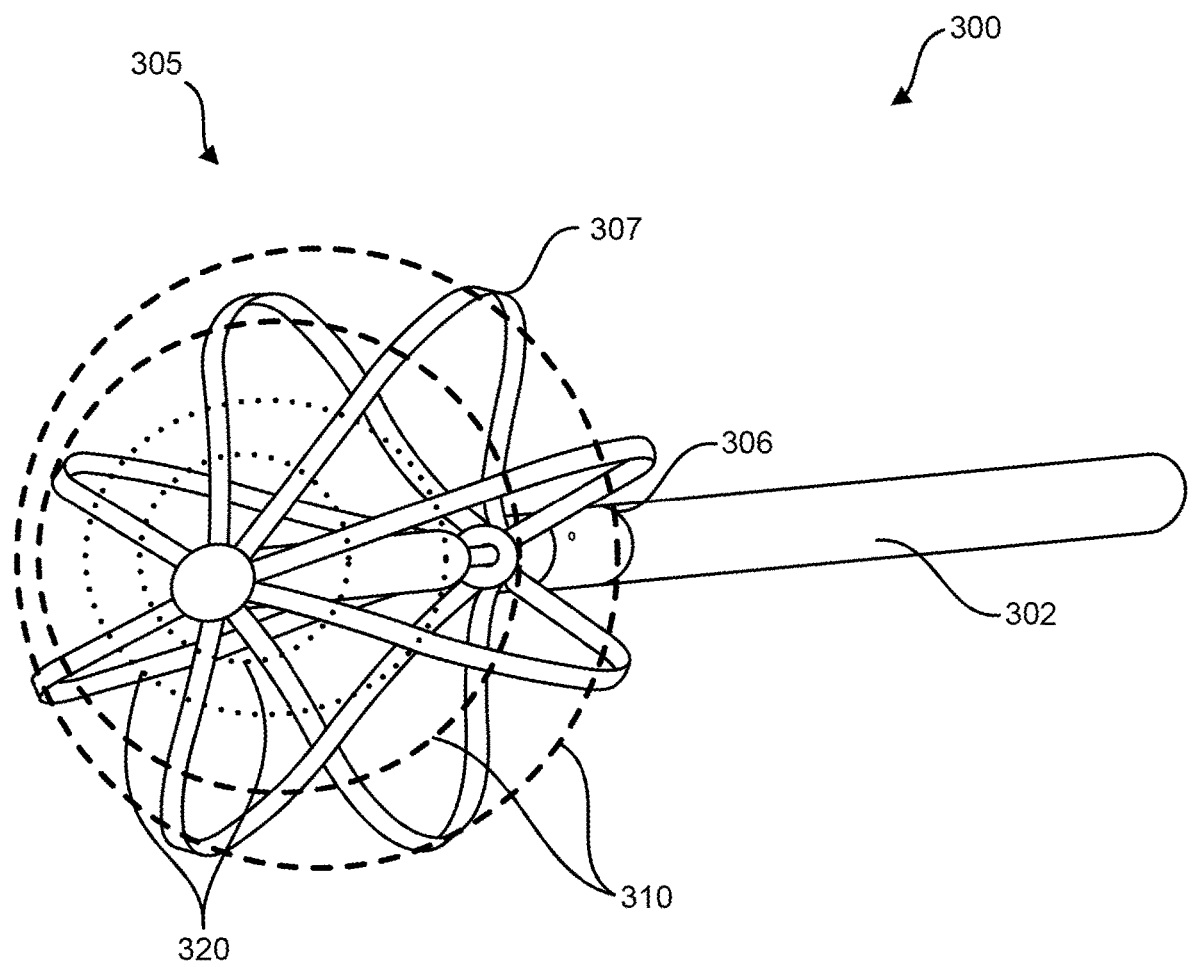
FIG. 3 is another diagram illustrating a hybrid electroporation ablation catheter, in accordance with embodiments of the subject matter of the disclosure

FIG. 3 is a diagram illustrating a hybrid electroporation ablation catheter 300, in accordance with embodiments of the subject matter of the disclosure. The catheter 300 includes an electrode assembly 305 extended from a distal end 306 of a catheter shaft 302. In the example illustrated, the electrode assembly 305 includes an expandable support structure 307 (e.g., a spline assembly as illustrated, although other expandable structures, e.g., inflatable balloon, may be used) a proximal first set of electrodes 310 disposed proximate the maximum diameter of the support structure 307, and, and a more distal second set of electrodes 320 disposed on the support structure 307 near its distal end.

As can be seen in FIG. 3, the proximal first set of electrodes 310 defines a ring of electrode pairs having a relatively large diameter, and can be suitable for forming relatively large substantially circumferential lesions, e.g., for isolating the pulmonary vein ostia in PVI procedures. In contrast, the distal second set of electrodes 320 defines a ring of electrode pairs having a relatively small diameter (compared to that formed by the first set of electrodes 310), and can be particularly configured for forming relatively small diameter focal ablation lesions on the cardiac chamber walls that may be delivered individually or sequentially through a series of energy deliveries to create a contiguous line of interconnected lesions forming a solid line of electrical conduction block.

In embodiments, the hybrid electroporation ablation catheter 300, the electrodes forming the first and second sets of electrodes 310, 320 are each individually addressable (e.g., by the controller 140 described above). As such, in some embodiments, the hybrid electroporation ablation catheter 300 has a first operation mode (e.g., circumferential ablation) and a second operation mode (e.g., focal ablation). In one example, the first set of electrodes 310 are activated and the second set of electrodes 320 are deactivated in the first operation mode. In one example, the first set of electrodes 310 are deactivated and the second set of electrodes 320 are activated in the second operation mode. The hybrid electroporation ablation catheter 300 thus provides the same dual-use capability as the electroporation ablation catheter 200 described above, but without requiring the user to change the geometry of the electrode assembly 305.

Figure 4:
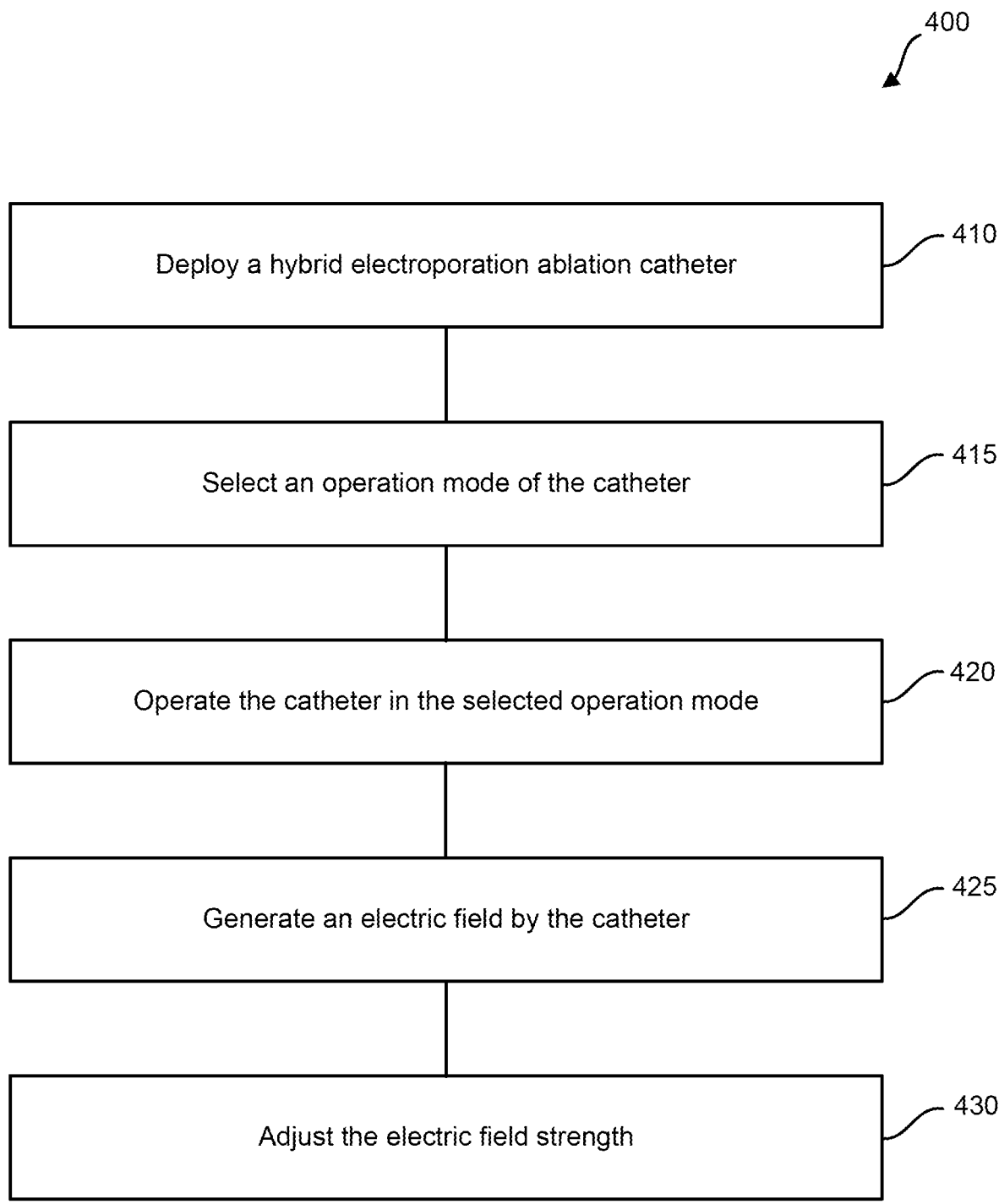
FIG. 4 is an example flow diagram depicting an illustrative method of using a hybrid electroporation ablation catheter, in accordance with some embodiments of the present disclosure.

FIG. 4 is an example flow diagram depicting an illustrative method 400 of using a hybrid electroporation ablation catheter, in accordance with some embodiments of the present disclosure. Aspects of embodiments of the method 400 may be performed, for example, by an electroporation ablation system/device (e.g., the system/device 100 depicted in FIG. 1). One or more steps of method 400 are optional and/or can be modified by one or more steps of other embodiments described herein. Additionally, one or more steps of other embodiments described herein may be added to the method 400. First, the electroporation ablation system/device deploys the hybrid electroporation ablation catheter proximate to a target tissue (410). In one embodiment, the hybrid electroporation ablation catheter is operable in a plurality of operation modes. In some cases, the plurality of operation modes includes a first operation mode and a second operation mode, where the hybrid electroporation ablation catheter is configured to deliver ablative energy to form circumferential ablation lesion in the first operation mode and configured to deliver ablative energy to form focal ablation lesion in the second operation mode.

In some cases, the hybrid electroporation ablation catheter includes a catheter shaft and an electrode assembly extending from a distal end of the catheter shaft. In one example, the electrode assembly comprises a plurality of electrodes. In some designs, at least one of the plurality of electrodes is deactivated in one of the plurality of operation modes. In some designs, the electrode assembly is configured to form a plurality of shapes in the plurality of operation modes, where the plurality of shapes have a different volume from each other. In some embodiment, the electrode assembly includes an inner shaft and a plurality of splines connected to the inner shaft, where the inner shaft is movable along the longitudinal axis of the catheter relative to the catheter shaft. In some cases, the electrode assembly is connected to or integrated with an actuator, which is configured to control the movement of the inner shaft relative to the catheter shaft.

In some embodiments, the electroporation ablation system/device selects an operation mode from the plurality of operation modes of the hybrid electroporation ablation catheter (415). In some cases, the operation mode can be selected automatically, for example, by a controller (e.g., the controller 140 in FIG. 1). In some cases, the operation mode is selected in response to sensing data collected by one or more sensors. In one embodiment, the operation mode is selected in response to sensing data indicating a position of the actuator.

In embodiments, the electroporation ablation system/device operates the hybrid electroporation ablation catheter in the selected operation mode (420), for example, in an operation mode for a specific ablation strategy (e.g., circumferential ablation, focal ablation, segment ablation, etc.). In some cases, the electroporation ablation system/device is configured to generate an electric field according to the selected operation mode by the hybrid electroporation ablation system/device (425), for example, generating the electric field at the electrodes of the catheter. In some cases, the generated electric field has an electric field strength sufficient for ablating target tissue via irreversible electroporation according to the selected operation mode. In some cases, the electroporation ablation system/device is configured to deliver exploration pulse to the electrodes.

In some cases, the electroporation ablation system/device is further configured to adjust the electric field (430), for example, by changing the exploration pulse and/or the activated electrodes. In one embodiment, a selected set of electrodes are activated. In some cases, the selected set of electrodes are disposed in a specific spatial pattern.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A hybrid electroporation ablation system, comprising:
   a hybrid electroporation ablation catheter, comprising:
      a catheter shaft having a proximal end and an opposite distal end;
      an inner shaft adapted to be extended from and retracted into the catheter shaft; and
      an electrode assembly coupled to the inner shaft and extending from the distal end of the catheter shaft, the electrode assembly comprising a plurality of splines, each spline of the plurality of splines including at least one proximal electrode and at least one distal electrode, wherein the electrode assembly is configured to be selectively manipulated between a first operation mode where the inner shaft is extended from the catheter shaft and a second operation mode where the inner shaft is at least partially retracted into the catheter shaft, the electrode assembly configured to form a first cavity in the first operation mode and a second cavity in the second operation mode, wherein the first cavity includes a first volume and the second cavity includes a second volume, the first volume being greater than the second volume,
a pulse generator configured to generate and deliver electroporation pulses to the hybrid electroporation ablation device, and
a controller coupled to the pulse generator and the electroporation ablation device,
wherein when in the first operation mode, the at least one proximal electrode and the at least one distal electrode are disposed distal to the distal end of the catheter shaft and are activated by the controller to deliver ablative energy with the electrode assembly, and, when operating in the second operation mode, the at least one distal electrode on each spline of the plurality of splines is disposed distal to the distal end of the catheter shaft and are activated by the controller to deliver the ablative energy with the electrode assembly, and the at least one proximal electrode of each spline of the plurality of splines is disposed within the catheter shaft and are deactivated by the controller.

2. The hybrid electroporation ablation system of claim 1, wherein in the first operation mode the electrode assembly is configured to deliver the ablative energy to form a circumferential ablation lesion having a diameter of between twenty millimeters and twenty-eight millimeters, and wherein in the second operation mode the electrode assembly is configured to deliver the ablative energy to form a focal ablation lesion having a diameter of between five millimeters and twenty millimeters.

3. The hybrid electroporation ablation system of claim 1, wherein the controller is configured to select one of the first operation mode or the second operation mode of the hybrid electroporation ablation device.

4. A method for electroporation ablations, the method comprising:
deploying an electrode assembly of a hybrid electroporation ablation catheter approximate to a target tissue, wherein the hybrid electroporation ablation catheter comprises a catheter shaft and an electrode assembly extending from a distal end of the catheter shaft, the electrode assembly having a plurality of splines, each spline of the plurality of splines including a proximal electrode and a distal electrode, the hybrid electroporation ablation catheter operable in a plurality of operation modes, the plurality of operation modes comprising a first operation mode and a second operation mode, the electrode assembly configured to form a first cavity in the first operation mode and a second cavity in the second operation mode, wherein the first cavity includes a first volume and the second cavity includes a second volume, the first volume being greater than the second volume;
selecting one of the first operation mode or the second operation mode from the plurality of operation modes of the hybrid electroporation ablation catheter, wherein the proximal electrode and distal electrode on each spline are disposed distal to the distal end of the catheter shaft in the first operation mode and where the distal electrode of each spline is disposed distal to the distal end of the catheter shaft and the proximal electrode of each spline is disposed within the catheter shaft in the second operation mode;
operating the hybrid electroporation ablation catheter in the selected operation mode wherein the proximal electrode and distal electrode on each spline of the plurality of splines are activated in the first operation mode and wherein the distal electrode on each spline is activated and the proximal electrode on each spline is deactivated in the second operation mode; and
generating an electric field at the electrode assembly of the hybrid electroporation catheter according to the selected operation mode, the electric field having an electric field strength sufficient for ablating the target tissue via irreversible electroporation to form a circumferential ablation lesion in the first operation mode and configured to deliver ablative energy to form a focal ablation lesion in the second operation mode.

5. The method of claim 4, wherein ablating the target tissue via irreversible electroporation to form the circumferential ablation lesion includes forming the circumferential ablation lesion to include a diameter of between twenty millimeters and twenty-eight millimeters, and wherein delivering the ablative energy to form the focal ablation lesion includes forming the focal ablation lesion to include a diameter of between five millimeters and twenty millimeters.

* * * * *